(12) United States Patent
Grosse

(10) Patent No.: US 9,877,822 B2
(45) Date of Patent: Jan. 30, 2018

(54) ENGINEERED TISSUE SCAFFOLDS AND SUPPORTS THEREFOR

(71) Applicant: Biostage, Inc., Holliston, MA (US)

(72) Inventor: Thomas Grosse, Holliston, MA (US)

(73) Assignee: Biostage, Inc., Holliston, MA (US)

( * ) Notice: Subject to any disclaimer, the term of this patent is extended or adjusted under 35 U.S.C. 154(b) by 441 days.

(21) Appl. No.: 13/869,949

(22) Filed: Apr. 24, 2013

(65) Prior Publication Data

US 2014/0107803 A1     Apr. 17, 2014

Related U.S. Application Data

(60) Provisional application No. 61/637,822, filed on Apr. 24, 2012, provisional application No. 61/639,846, filed on Apr. 27, 2012.

(51) Int. Cl.
*A61F 2/02* (2006.01)
*A61F 2/04* (2013.01)
(Continued)

(52) U.S. Cl.
CPC .................. *A61F 2/02* (2013.01); *A61F 2/04* (2013.01); *C12M 21/08* (2013.01); *C12M 25/14* (2013.01); *C12N 5/0068* (2013.01); *A61F 2/20* (2013.01); *A61F 2002/043* (2013.01); *A61F 2002/046* (2013.01); *A61F 2240/004* (2013.01); *F04C 2270/041* (2013.01)

(58) Field of Classification Search
CPC .......... A61F 2240/004; A61F 2240/002; A61F 2240/005; A61F 2240/007; A61F 2/02; A61F 2230/0034; A61F 2230/0064; A61F 2230/0008; A61F 2002/043; A61F 2002/046; A61F 2/20; A61F 2/203; A61F 2230/006; A61F 2002/096; C12M 21/08; D01D 5/0007; D01D 5/0084; D01D 5/24; D01D 5/253; A61L 2430/22
USPC ................ 623/23.72, 9; 428/399, 397, 398; 264/465; 435/395, 396
See application file for complete search history.

(56) References Cited

U.S. PATENT DOCUMENTS 2,625,054 A * 1/1953 Bauman .................... G05G 1/12
                                                       403/357
2,745,689 A * 5/1956 Balint ....................... G05G 1/12
                                                       403/357
(Continued)

FOREIGN PATENT DOCUMENTS

CN      1974750 A    6/2007
EP      0610423 A1   8/1994
(Continued)

OTHER PUBLICATIONS

Bouffi et al., The role of pharmacologically active microcarriers releasing TGF-beta3 in cartilage formation in vivo by mesenchymal stem cells. Biomaterials. Sep. 2010;31(25):6485-93. doi: 10.1016/j.biomaterials.2010.05.013. Epub Jun. 8, 2010.
(Continued)

*Primary Examiner* — Jonathan Miles
*Assistant Examiner* — Majid Jamialahmadi
(74) *Attorney, Agent, or Firm* — Young Basile Hanlon & MacFarlane, P.C.

(57) ABSTRACT

According to some aspects, supports are provided for producing artificial tissue scaffolds.

4 Claims, 5 Drawing Sheets

(51) Int. Cl.
  *C12M 3/00* (2006.01)
  *C12N 5/00* (2006.01)
  *C12M 1/12* (2006.01)
  *A61F 2/20* (2006.01)

(56) References Cited

U.S. PATENT DOCUMENTS

| | | | |
|---|---|---|---|
| 4,043,331 A * | 8/1977 | Martin | A61L 15/24 264/413 |
| 4,237,746 A * | 12/1980 | Rossi | F16B 17/006 29/512 |
| 5,032,508 A | 7/1991 | Naughton et al. | |
| 5,160,490 A | 11/1992 | Naughton et al. | |
| 5,266,480 A | 11/1993 | Naughton et al. | |
| 5,399,665 A | 3/1995 | Barrera et al. | |
| 5,433,909 A | 7/1995 | Martakos et al. | |
| 5,443,950 A | 8/1995 | Naughton et al. | |
| 5,478,739 A | 12/1995 | Slivka et al. | |
| 5,512,475 A | 4/1996 | Naughton et al. | |
| 5,514,378 A | 5/1996 | Mikos et al. | |
| 5,516,680 A | 5/1996 | Naughton et al. | |
| 5,516,681 A | 5/1996 | Naughton et al. | |
| 5,518,915 A | 5/1996 | Naughton et al. | |
| 5,541,107 A | 7/1996 | Naughton et al. | |
| 5,578,485 A | 11/1996 | Naughton et al. | |
| 5,602,026 A | 2/1997 | Dunn et al. | |
| 5,624,840 A | 4/1997 | Naughton et al. | |
| 5,677,355 A | 10/1997 | Shalaby et al. | |
| 5,759,830 A | 6/1998 | Vacanti et al. | |
| 5,770,193 A | 6/1998 | Vacanti et al. | |
| 5,770,417 A | 6/1998 | Vacanti et al. | |
| 5,785,964 A | 7/1998 | Naughton et al. | |
| 5,792,603 A | 8/1998 | Dunkelman et al. | |
| 5,800,537 A | 9/1998 | Bell | |
| 5,855,610 A | 1/1999 | Vacanti et al. | |
| 5,858,721 A | 1/1999 | Naughton et al. | |
| 5,863,531 A | 1/1999 | Naughton et al. | |
| 5,902,741 A | 5/1999 | Purchio et al. | |
| 5,916,265 A | 6/1999 | Hu | |
| 5,928,945 A | 7/1999 | Seliktar et al. | |
| 6,008,049 A | 12/1999 | Naughton et al. | |
| 6,022,743 A | 2/2000 | Naughton et al. | |
| 6,087,552 A | 7/2000 | Gregory | |
| 6,140,039 A | 10/2000 | Naughton et al. | |
| 6,372,495 B1 | 4/2002 | Flendrig | |
| 6,376,244 B1 | 4/2002 | Atala | |
| 6,379,956 B1 | 4/2002 | Bader | |
| 6,416,995 B1 | 7/2002 | Wolfinbarger | |
| 6,428,802 B1 | 8/2002 | Atala | |
| 6,537,567 B1 | 3/2003 | Niklason et al. | |
| 6,960,427 B2 | 11/2005 | Haverich et al. | |
| 6,962,814 B2 | 11/2005 | Mitchell et al. | |
| 7,316,822 B2 | 1/2008 | Binette et al. | |
| 7,371,400 B2 | 5/2008 | Borenstein et al. | |
| 7,531,503 B2 | 5/2009 | Atala et al. | |
| 7,662,409 B2 | 2/2010 | Masters | |
| 7,829,108 B2 | 11/2010 | Van Dyke et al. | |
| 8,057,535 B2 | 11/2011 | Hashi et al. | |
| 8,221,777 B2 | 7/2012 | Van Dyke et al. | |
| 8,470,520 B2 | 6/2013 | Ott et al. | |
| 8,507,263 B2 | 8/2013 | Asnaghi et al. | |
| 2002/0115208 A1 | 8/2002 | Mitchell et al. | |
| 2002/0172705 A1 | 11/2002 | Murphy et al. | |
| 2002/0182241 A1 | 12/2002 | Borenstein et al. | |
| 2002/0182261 A1 | 12/2002 | Dai et al. | |
| 2003/0021827 A1 | 1/2003 | Malaviya et al. | |
| 2003/0024534 A1 | 2/2003 | Silvestri et al. | |
| 2003/0087428 A1 | 5/2003 | Wolfinbarger, Jr. et al. | |
| 2003/0100108 A1 | 5/2003 | Altman et al. | |
| 2003/0124099 A1 | 7/2003 | Atala | |
| 2003/0129736 A1 | 7/2003 | Mitrani | |
| 2003/0129751 A1 | 7/2003 | Grikscheit et al. | |
| 2003/0166274 A1 | 9/2003 | Hewitt et al. | |
| 2004/0044403 A1 | 3/2004 | Bischoff et al. | |
| 2004/0058440 A1 | 3/2004 | Brown et al. | |
| 2004/0110285 A1 | 6/2004 | Lendlein et al. | |
| 2005/0003535 A1 | 1/2005 | Gerlach | |
| 2005/0009178 A1 | 1/2005 | Yost et al. | |
| 2005/0013870 A1 | 1/2005 | Freyman et al. | |
| 2005/0107868 A1 | 5/2005 | Nakayama et al. | |
| 2005/0196423 A1 | 9/2005 | Batich et al. | |
| 2005/0203636 A1 | 9/2005 | McFetridge | |
| 2005/0209687 A1 | 9/2005 | Sitzmann et al. | |
| 2005/0256588 A1 | 11/2005 | Sawa et al. | |
| 2006/0035376 A1 | 2/2006 | Geltser | |
| 2006/0084759 A1 | 4/2006 | Calabro et al. | |
| 2006/0141012 A1 | 6/2006 | Gingras | |
| 2006/0204441 A1 | 9/2006 | Atala et al. | |
| 2006/0204445 A1 | 9/2006 | Atala et al. | |
| 2006/0204539 A1 | 9/2006 | Atala et al. | |
| 2006/0239981 A1 | 10/2006 | Yoo et al. | |
| 2006/0240061 A1 | 10/2006 | Atala et al. | |
| 2006/0253192 A1 | 11/2006 | Atala et al. | |
| 2006/0257377 A1 | 11/2006 | Atala et al. | |
| 2006/0258004 A1 | 11/2006 | Kosnik et al. | |
| 2007/0005139 A1 | 1/2007 | Vacanti et al. | |
| 2007/0059293 A1 | 3/2007 | Atala | |
| 2008/0112995 A1 | 5/2008 | Shalev | |
| 2008/0131473 A1 | 6/2008 | Brown et al. | |
| 2008/0145920 A1 | 6/2008 | Bouten et al. | |
| 2008/0260831 A1 | 10/2008 | Badylak et al. | |
| 2008/0274545 A1 | 11/2008 | Kuo et al. | |
| 2008/0292677 A1 | 11/2008 | Cortiella et al. | |
| 2009/0035855 A1 | 2/2009 | Ying et al. | |
| 2009/0060961 A1 | 3/2009 | Naruse et al. | |
| 2009/0075282 A1 | 3/2009 | Mahmood et al. | |
| 2009/0142836 A1 | 6/2009 | Wang et al. | |
| 2009/0265005 A1 | 10/2009 | Yoo et al. | |
| 2010/0034791 A1 | 2/2010 | Lelkes et al. | |
| 2010/0061962 A1 | 3/2010 | Li | |
| 2010/0093066 A1 | 4/2010 | Taylor et al. | |
| 2010/0129450 A1 | 5/2010 | Atala et al. | |
| 2010/0148404 A1 | 6/2010 | Smida et al. | |
| 2010/0233115 A1 | 9/2010 | Patel et al. | |
| 2010/0292791 A1 | 11/2010 | Lu et al. | |
| 2011/0033918 A1 | 2/2011 | Asnaghi et al. | |
| 2011/0039101 A1 * | 2/2011 | Chang | D01D 5/0007 428/398 |
| 2011/0046732 A1 | 2/2011 | Dyke et al. | |
| 2011/0130826 A1 * | 6/2011 | Cragg | A61F 2/07 623/1.15 |
| 2011/0160846 A1 | 6/2011 | Bishop et al. | |
| 2011/0224800 A1 | 9/2011 | Ludlow et al. | |
| 2011/0250688 A1 | 10/2011 | Hasan | |
| 2012/0068384 A1 | 3/2012 | Phaneuf et al. | |
| 2012/0135234 A1 | 5/2012 | Netravali et al. | |
| 2012/0141439 A1 | 6/2012 | Ott | |
| 2012/0183944 A1 | 7/2012 | Taylor et al. | |
| 2012/0259415 A1 | 10/2012 | Van Dyke et al. | |
| 2012/0271405 A1 | 10/2012 | Soletti et al. | |
| 2012/0324975 A1 * | 12/2012 | Anderson | A61B 17/064 72/324 |
| 2012/0330437 A1 | 12/2012 | El-Kurdi et al. | |
| 2013/0030548 A1 | 1/2013 | Ling | |
| 2013/0041265 A1 | 2/2013 | Sostek et al. | |
| 2013/0109088 A1 | 5/2013 | Ott et al. | |
| 2013/0177972 A1 | 7/2013 | Green et al. | |
| 2013/0204288 A1 | 8/2013 | Johnson et al. | |
| 2013/0251687 A1 | 9/2013 | Christman et al. | |
| 2014/0058508 A1 * | 2/2014 | Seifalian | A61F 2/04 623/9 |
| 2014/0124670 A1 | 5/2014 | Sostek | |
| 2014/0141152 A1 | 5/2014 | Sostek et al. | |
| 2014/0141552 A1 | 5/2014 | Sostek et al. | |
| 2014/0377848 A1 | 12/2014 | Zink et al. | |
| 2014/0377863 A1 | 12/2014 | Seifalain et al. | |
| 2015/0011892 A1 | 1/2015 | Sostek et al. | |
| 2015/0064142 A1 | 3/2015 | Green et al. | |
| 2015/0359621 A1 | 12/2015 | Sostek | |

(56) References Cited

U.S. PATENT DOCUMENTS

| | | |
|---|---|---|
| 2016/0040107 A1 | 2/2016 | Hedberg |
| 2016/0053213 A1 | 2/2016 | Hedberg |

FOREIGN PATENT DOCUMENTS

| | | |
|---|---|---|
| WO | WO 1995/025550 A1 | 9/1995 |
| WO | WO 1996/008213 A1 | 3/1996 |
| WO | WO 2000/59618 A1 | 10/2000 |
| WO | WO 2005/063316 A1 | 7/2005 |
| WO | WO 2006/099315 A2 | 9/2006 |
| WO | WO 2006/099332 A2 | 9/2006 |
| WO | WO 2006/099333 A2 | 9/2006 |
| WO | WO 2006/099334 A2 | 9/2006 |
| WO | WO 2006/099372 A2 | 9/2006 |
| WO | WO 2006/099373 A2 | 9/2006 |
| WO | WO 2007/025233 A1 | 3/2007 |
| WO | WO 2007/124127 A2 | 11/2007 |
| WO | WO 2008/100534 A2 | 8/2008 |
| WO | WO 2010/141803 A2 | 12/2010 |
| WO | WO 2011/084559 A2 | 7/2011 |
| WO | WO 2012/080390 A1 | 6/2012 |
| WO | WO 2013/056049 A2 | 4/2013 |
| WO | WO 2013/155488 A2 | 10/2013 |

OTHER PUBLICATIONS

Chen et al., Formation of lung alveolar-like structures in collagen-glycosaminoglycan scaffolds in vitro. Tissue Eng. Sep.-Oct. 2005;11(9-10):1436-48.

Conconi et al., Tracheal matrices, obtained by a detergent-enzymatic method, support in vitro the adhesion of chondrocytes and tracheal epithelial cells. Transpl Int. Jun. 2005;18(6):727-34.

Cortiella et al., Tissue-engineered lung: an in vivo and in vitro comparison of polyglycolic acid and pluronic F-127 hydrogel/somatic lung progenitor cell constructs to support tissue growth. Tissue Eng. May 2006;12(5):1213-25.

De Mel et al., In situ endothelialization potential of a biofunctionalised nanocomposite biomaterial-based small diameter bypass graft. Biomed Mater Eng. 2009;19(4-5):317-31. doi: 10.3233/BME-2009-0597.

Doshi et al., Electrospinning process and applications of electrospun fibers. J Electrostat. Aug. 1995;35(2-3):151-60. Selected papers from 1993 IEEE Industry Applications Society Meeting "Electrostatics in Polymer Processing and Charge Monitoring."

Hoganson et al., Tissue engineering and organ structure: a vascularized approach to liver and lung. Pediatr Res. May 2008;63(5):520-6. doi: 10.1203/01.pdr.0000305879.38476.0c.

Ingenito et al., Design and testing of biological scaffolds for delivering reparative cells to target sites in the lung. J Tissue Eng Regen Med. Jun. 2010;4(4):259-72. doi: 10.1002/term.237.

Kannan et al., Silsesquioxane nanocomposites as tissue implants. Plast Reconstr Surg. May 2007;119(6):1653-62.

Kannan et al., The antithrombogenic potential of a polyhedral oligomeric silsesquioxane (POSS) nanocomposite. Biomacromolecules. Jan. 2006;7(1):215-23. Epub Nov. 15, 2005.

Kannan et al., The endothelialization of polyhedral oligomeric silsesquioxane nanocomposites: an in vitro study. Cell Biochem Biophys. 2006;45(2):129-36.

Kidane et al., A novel nanocomposite polymer for development of synthetic heart valve leaflets. Acta Biomater. Sep. 2009;5(7):2409-17. doi: 10.1016/j.actbio.2009.02.025. Epub Feb. 21, 2009.

Li et al., A single-use, scalable perfusion bioreactor system. BioProcess International. Jun. 2009;7(6):46-54 (even pages). Epub May 2009.

Lin et al., Biocompatibility of poly-DL-lactic acid (PDLLA) for lung tissue engineering. J Biomater Appl. Oct. 2006;21(2):109-18. Epub Jan. 27, 2006.

MacChiarini et al., Clinical transplantation of a tissue-engineered airway. The Lancet. Dec. 13, 2008;372(9655):2023-30. Epub Nov. 19, 2008.

Nichols et al., Engineering of a complex organ: progress toward development of a tissue-engineered lung. Proc Am Thorac Soc. Aug. 15, 2008;5(6):723-30. doi: 10.1513/pats.200802-022AW.

Rashid et al., Tissue engineering of a hybrid bypass graft for coronary and lower limb bypass surgery. FASEB J. Jun. 2008;22(6):2084-9. doi: 10.1096/fj.07-096586. Epub Jan. 18, 2008.

Reneker et al., Nanometre diameter fibres of polymer, produced by electrospinning. Nanotechnol. Sep. 1996;7(3):216-23.

Sato et al., Replacement of the left main bronchus with a tissue-engineered prosthesis in a canine model. Ann Thorac Surg. Aug. 2008;86(2):422-8. doi: 10.1016/j.athoracsur.2008.04.015.

Teebken et al., Tissue engineering of vascular grafts: human cell seeding of decellularised porcine matrix. Eur J Vasc Endovasc Surg. Apr. 2000;19(4):381-6.

Vasita et al., Nanofibers and their applications in tissue engineering. Int J Nanomedicine. 2006;1(1):15-30.

Jungebluth et al., Tracheobronchial transplantation with a stem-cell-seeded bioartificial nanocomposite: a proof-of-concept study. Lancet. Dec. 10, 2011;378(9808):1997-2004. doi: 10.1016/S0140-6736(11)61715-7. Epub Nov. 24, 2011.

\* cited by examiner

Ratio ~1:4

Ratio ~1:3

Ratio ~1:2

ENGINEERED TISSUE SCAFFOLDS AND SUPPORTS THEREFOR

RELATED APPLICATIONS

This application claims priority under 35 U.S.C. §119(e) of U.S. Provisional Patent Application No. 61/637,822, filed on Apr. 24, 2012 and entitled "SUPPORTS FOR ARTIFICIAL TISSUE SCAFFOLDS," and U.S. Provisional Patent Application No. 61/639,846, filed on Apr. 27, 2012 and entitled "AIRWAY SCAFFOLDS." Each of these applications is incorporated herein by reference in its entirety for all purposes.

BACKGROUND

Tissue engineering can involve generating a synthetic scaffold and seeding the scaffold to produce an engineered tissue that can be implanted into a subject. Different techniques have been used for producing synthetic scaffolds. Often scaffolds have been produced on a one-off basis for a particular clinical application or research investigation. However, suitable systematic approaches that can be widely implemented for the commercial production of tissues are lacking.

SUMMARY

According to some aspects of the invention, supports for synthetic tissue scaffolds are provided. In some embodiments, a support comprises a first tubular region. In some embodiments, the supports comprise a first tubular region connected to a second tubular region, wherein the first region has a different cross-section than the second region. In some embodiments, the transition from the first region to the second region is gradual, linear, or exponential. In some embodiments, the first region has a cross-section as shown in FIG. 1C. In some embodiments, the second region has a cross-section as shown in FIG. 1A. In some embodiments, the support is made partially or entirely of conductive material (e.g., metal).

In some embodiments, a support for an artificial tissue scaffold comprises an elongate member (e.g., a tube-like or rod-like member) having, along its length, transverse cross-sections having an outer perimeter defining a convex, curvilinear region separated by (e.g., surrounding or interrupted by) a substantially flat perimeter region, wherein the transition from the convex, curvilinear perimeter region to the substantially flat perimeter region is a substantially smooth transition (e.g., at one or both ends of the substantially flat perimeter region). In some embodiments, the transverse cross-sections have bilateral symmetry, wherein the axis of symmetry passes perpendicularly through the midpoint of the substantially flat perimeter region. In some embodiments, the length of the substantially flat perimeter region is smaller than the maximum outer dimension of the convex, curvilinear region along an axis parallel to the substantially flat perimeter region. In some embodiments, the transverse cross-sections are as shown in FIG. 1C.

In some embodiments, the supports have a reduced microbiological load (e.g., they are manufactured or prepared in an environment with reduced microbiological load). In some embodiments, the supports are aseptic. Aseptic supports may be produced, for example, by autoclaving or exposure to gamma irradiation or any other suitable method. In some embodiments, the supports are made partially or entirely of a conductive material (e.g., a conductive metal).

Further aspects of the invention provide kits that comprise one or more supports, for example, in an container or package (e.g., a sterile container or package). In some embodiments, the kits comprise a plurality supports having similar transverse cross-sectional profiles (e.g., a cross-sectional profile of FIG. 1A, 1B, 1C, or 1D) of different size scales.

According to some aspects of the invention, methods are provided for producing an artificial (e.g., synthetic) tissue scaffold using any of the supports disclosed herein. In some embodiments, the methods comprise obtaining a support and depositing a synthetic and/or natural material on the support such that the synthetic or natural material forms a scaffold having an inner surface geometry (size and shape) that corresponds to the outer surface of the support. The synthetic or natural material may be deposited on the support by any suitable means. In some embodiments, the synthetic or natural material is deposited by electrospinning. Any suitable synthetic or natural material may be used for producing the scaffold. In some embodiments, the synthetic material comprises polyurethane and/or polyethylene terephthalate. In some embodiments, after the synthetic and/or natural material has formed (e.g., has set, hardened, dried, polymerized, or otherwise formed a stable structure on the support) the support is removed to produce the scaffold that can be subsequently manipulated (e.g., cellularized, etc.).

In some embodiments, a support is used to produce a synthetic tissue scaffold that includes one or a plurality of ribs or other suitable support component placed or deposited on the elongate member (e.g., on an initial layer of scaffold material on the elongate member). In some embodiments, the plurality of ribs are spaced along the length of the elongate member.

In some embodiments, each rib is placed or deposited such that the ends of each rib are positioned between the maximum outer dimension of the convex, curvilinear region and the substantially flat perimeter region of a transverse cross-section of the elongate member. In some embodiments, each rib is placed or deposited such that the ends of each rib are positioned as depicted in FIG. 6.

According to some aspects of the invention, methods are provided for producing an engineered tissue that comprise obtaining an synthetic tissue scaffold (e.g., a scaffold produced as disclosed herein), seeding cells on the scaffold, and maintaining the cells on the scaffold under conditions suitable for promoting cell viability, growth, development, and/or synthesis of an artificial tissue by the cells. It should be appreciated that the cellularization process does not need to result in complete cellularization of the scaffold and/or differentiation of the cells. In many embodiments, a cellularized scaffold (e.g., a scaffold that has an appropriate and/or sufficient number of cells attached to its surface) can be transplanted into a subject where further cellularization and cell differentiation occurs. It should be appreciated that in some embodiments, a synthetic scaffold that has not been cellularized can be transplanted into a host and cellularization can occur in the host. However, it most embodiments, an ex vivo cellularization is performed prior to transplantation into the recipient.

In some embodiments, a support is configured and arranged for synthesizing a tissue scaffold shaped as a portion of an airway. In some embodiments, the portion of the airway is a subglottis, a trachea, or a bronchial stem or a transition region of the airway, or a portion of one or more thereof, or any combination thereof. In some embodiments, the portion of the airway comprises a portion of a subglottic region connected to a portion of a tracheal region (e.g., including a transition region). In some embodiments, the methods further comprise obtaining the cells from a subject (e.g., a subject who is the intended recipient of the artificial tissue).

It should be appreciated that a support described herein is typically removed from a scaffold that was synthesized on the support prior to cellularization of the scaffold. However, in some embodiments, certain cellularization steps may be performed on a scaffold that is still on a support.

According to some aspects of the invention, methods are provided for replacing a damaged tissue in a subject. In some embodiments, methods comprise producing an engineered tissue (e.g., an artificial tissue produced according to the methods disclosed herein), performing a surgical procedure to extract the damaged tissue from the subject, and replace the damaged tissue with the engineered tissue.

According to some aspects of the invention, an artificial cricoid cartilage is provided. In some embodiments, the artificial cricoid cartilage has a ratio of ventral to dorsal height of less than 1:1. In some embodiments, the artificial cricoid cartilage is disposed around a transition region between a subglottic region and a tracheal region.

These and other aspects are described in more detail herein.

DETAILED DESCRIPTION OF CERTAIN EMBODIMENTS

Figure 1A:
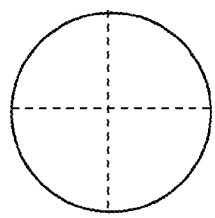
FIG. 1A-E are non-limiting schematic drawings of examples of cross-sections of a support for artificial tissue scaffolds.
Figure 1B:
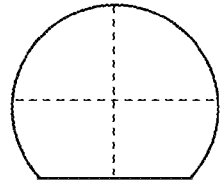

In some embodiments, aspects of the invention relate to methods, compositions, and articles (e.g., supports) for producing artificial (e.g., synthetic) tissues, organs, or portions thereof that can be implanted into a host (e.g., a human host) to replace diseased or injured tissues, organs, or portions thereof.

In some embodiments, aspects of the invention relate to supports for artificial scaffolds that are used for tissue growth. Scaffolds generated as described herein can be seeded with appropriate cell types to produce artificial tissues or organs or portions thereof for transplantation into a host (e.g., a human host). It should be appreciated that techniques and materials described herein can be used to produce any suitable size or shape of support to form any size or shape artificial scaffold (e.g., planar structures, tubular structures, hollow structures, solid structure, complex structures) any of which can have one or more dimensions ranging for example from about 1 mm to 50 cms (for example tracheal regions of several cms in length). However, larger, smaller, or intermediate sized structures may be made as described herein.

In some embodiments, a support comprises an elongate member having a shape that corresponds to the inner geometry of a synthetic (e.g., artificial) scaffold that will be produced on the support (e.g., corresponding to the inner geometry of a synthetic tracheal scaffold). In some embodiments, a support for producing an artificial scaffold can be a mandrel, tube, or any other shaped support upon which scaffold material can be deposited. It should be appreciated that any technique can be used to deposit a scaffold material. A scaffold material can include one or more synthetic materials (e.g., synthetic polymers), one or more natural materials (e.g., materials derived from a natural scaffold), or a combination of one or more of each thereof. In some embodiments, a support is a conductive mandrel and the scaffold material is deposited via electrospinning.

It should be appreciated that the support can include one or more regions having any suitable geometry (e.g., size or shape), e.g., U-shaped, C-shaped, S-shaped, O-shaped, or other simple or complex shapes, for example in cross-section (e.g., in transverse cross-section). However, in some embodiments, the size and shape of the support is designed to produce a scaffold that will support an artificial tissue of the same or similar size as the tissue being replaced or supplemented in a host (e.g., trachea or other airway portion, blood vessel, liver or kidney region, or other tissue or organ). In some embodiments, the size and shape of the support is determined from patient data, e.g., a CT scan, other X-ray data, bronchoscopic data, one or more intra-operative measurements taken by a surgeon, or biostatistical data based on age, weight, gender, etc., for example, or a combination of any two or more of the foregoing.

In some embodiments, supports are tubular. It should be appreciated that a tubular region can be a cylinder with a uniform diameter. However, in some embodiments, a tubular region can have any appropriate tubular shape (for example, including portions with different diameters along the length of the tubular region and different cross-sectional shapes). In some embodiments, a tubular support can be a solid mandrel (e.g., a mandrel that can be used for electrospinning). In some embodiments, a tubular support can have one or more hollow regions. In some embodiments, regardless of whether the support is solid or has one or more hollow regions, a cross-section of a tubular support can be circular or any other suitable shape. For example, a cross-section (e.g., a transverse cross-section) can be D-shaped, C-shaped, U-shaped, horseshoe-shaped, elliptical, or approximately one of these shapes, or any other shape, for example a shape as shown in FIG. 1. In some embodiments, the support is useful for producing tissue scaffolds having regions of differing cross-sectional geometries. In such embodiments, the support may comprise two regions (or more than two regions) each having a different cross-sectional geometry and a transition zone between the regions. In some embodiments, the transition zone of a support comprises an abrupt change between two different cross-sectional geometries. However, in some embodiments, the transition zone comprises a gradual or continuous change from one cross-sectional geometry to another. In some embodiments, the support comprises a transition zone between regions of differing cross-sectional geometries that is suitable for producing a tissue scaffold having geometric features of the transition from a tracheal region to a subglottic region of an airway, which may include the cricoid cartilage region of an airway. In some embodiments, scaffold regions produced on the different regions of the support may be seeded with different cells or treated with different media, growth factors, or cytokines, or otherwise prepared in such a way as to produce tissue scaffolds having different physicochemical and/or biological properties as well as different cross-sectional geometries. However, in some embodiments, scaffold regions produced on the different regions of the support are treated similarly and/or seeded with the same cell types as aspects of the invention are not limited in this respect.

Figure 1C:
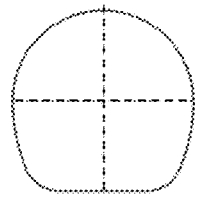
Figure 1D:
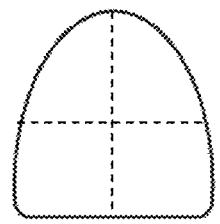

In some embodiments, a support for an artificial tissue scaffold comprises an elongate member (e.g., a tube-like or rod-like member) having, along its length, transverse cross-sections having an outer perimeter defining a convex, curvilinear region separated by (e.g., surrounding or interrupted by) a flat or substantially flat perimeter region, wherein the transition from the convex, curvilinear perimeter region to the flat or substantially flat perimeter region is a substantially smooth transition (e.g., at one or both ends of the flat or substantially flat perimeter region). In some embodiments, the transverse cross-sections have bilateral symmetry, wherein the axis of symmetry passes perpendicularly through the midpoint of the substantially flat perimeter region. In some embodiments, the length of the substantially flat perimeter region is smaller than the maximum outer dimension of the convex, curvilinear region along an axis parallel to the substantially flat perimeter region. In some embodiments, the transverse cross-sections are as shown in FIG. 1C.

In some embodiments, the dimension of the tubular support along its longitudinal axis is at least 5 cm. In some embodiments, the dimension of the tubular support along the longitudinal axis is at least 10 cm, 15 cm, 20 cm, or more. In some embodiments, the dimensions of each of the major and minor axes of a cross-section of a tubular support (e.g., of a transverse cross-section of a tubular support) are at least about 50 mm, at least about 100 mm, at least about 500 mm, or at least about 1 cm. In some embodiments, the dimensions of each of the major and minor axes of the cross-section of a tubular support are up to 250 mm, up to 500 mm, up to 1 cm, up to 2 cm. In some embodiments, the dimensions of the major and minor axes of the cross-section of the support are each at least about 0.5 cm. In some embodiments, the dimensions of the major and minor axes of the cross-section of the support are each at least about 1.5 cm. In some embodiments, the dimensions of the major and minor axis of the cross-section of the support are each at least about 2 cm. In some embodiments, the dimensions of the major and minor axes of the cross-section of the support are in a range of 0.5 cm to 1.5 cm. In some embodiments, the dimensions of the major and minor axes of the cross-section of the support are in a range of 1 cm to 2 cm. It should be appreciated that for many cross-sectional shapes, the major axis will be longer than the minor axis (for example, about 5% longer, about 10% longer, about 25% longer, about 50% longer, or more). If the cross-section is roughly ellipsoid in shape, the major and minor axis can be defined as a line passing through the foci, center, and vertices of the cross-section. The minor axis is perpendicular to the major axis and also passes through the center of the cross-section. If the cross-section is not roughly circular or ellipsoid, the major axis can be defined as the longest axis of the shape passing through the center of the shape, with the minor axis perpendicular to this axis and also passing through the center of the shape. For example, the dotted lines in FIG. 1 show the axes used to roughly calculate the dimensions of the cross-section. However, it should be appreciated that in some embodiments one or more regions of a support can have a circular or substantially circular cross-sectional geometry (e.g., a circular transverse cross-section).

Accordingly, in some embodiments, a portion of the cross-section (e.g., a transverse cross-section) of a tubular support is straight (e.g., flat or substantially flat) and the remainder is part of a circle, oval, ellipse, or other structure (for example, the cross-section may be D-shaped) or combination of two or more thereof. In some embodiments, a tubular support has a cross-section of FIG. 1A, B, C, or D. In some embodiments, the flat or substantially flat portion of the support corresponds to the dorsal side of an airway region (e.g., a tracheal region) and the opposing side corresponds to the ventral side. Accordingly, the resulting shape of a scaffold produced on the structure corresponds to an airway region having dorsal and ventral sides.

In some embodiments, the dimensions and/or shape of the cross-section of the support change over the length of the support. In some embodiments, the support has at least two regions, wherein the first region has a first cross-sectional geometry (e.g., first shape and size) and wherein the second region has a second cross-sectional geometry (e.g., second shape and size). It should be appreciated that the change from the first region to the second region can be abrupt or can be gradual (e.g., to reduce sharp edges). In some embodiments, a transition region is located between first and second regions (or portions thereof) that are required to be replaced in a subject.

Figure 6A:
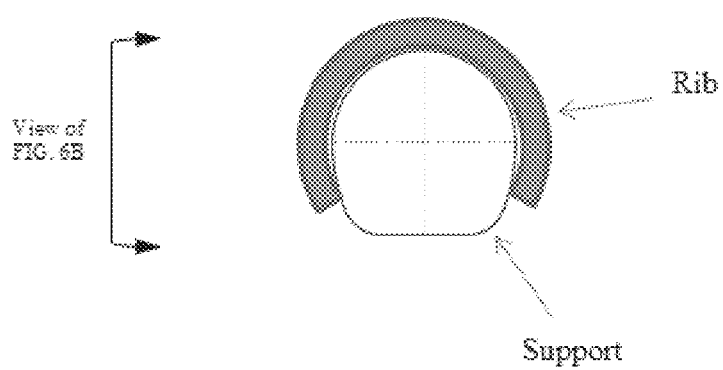
FIG. 6 illustrates a non-limiting embodiment of a support for a tissue scaffold with a plurality of ribs of the tissue scaffold shown (in transverse cross-section in FIG. 6A, and in longitudinal side view in FIG. 6B).
Figure 6B:
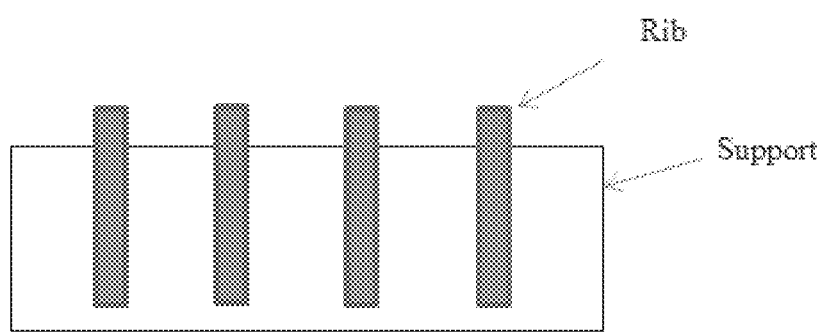

In some embodiments, the surface of the support is sufficiently smooth to prevent cutting or tearing or puncturing of the tissue scaffold produced on the support. In some embodiments, the shape of the support is designed to produce a scaffold that does not damage (e.g., cut, tear, or puncture) surrounding tissue after implantation into a patient. In some embodiments, the outer perimeter of a cross-section (e.g., transverse cross-section) of one or more regions of a support does not include any sharp transitions that could produce sharp edges or protrusions in a scaffold that could become damaging to surrounding tissue after implantation. In some embodiments, the cross-sectional shape of one or more regions of a support (e.g., mandrel) is designed to reduce the likelihood that a support rib or other structural feature that is incorporated into a synthetic scaffold will protrude into surrounding tissue after implantation. In some embodiments, a scaffold that is electrospun on the surface of a mandrel is reinforced by incorporating one or more structural components or ribs (e.g., that are thicker, and/or made of different material than the more flexible and/or thinner regions of the synthetic scaffold). These structural components or ribs can be electrospun in place. However, in some embodiments, they are produced separately (e.g., using any suitable technique, including electrospinning, casting, molding, etc., or any combination thereof) and added to the surface of the scaffold or incorporated in between a first and a second layer of electrospun scaffold material. These structural components of the scaffold can have any suitable pattern or shape. However, in some embodiments, they are ribs or other components shaped as incomplete circles or loops of thicker material that that are placed or deposited onto or incorporated into the scaffold to mimic the cartilaginous supports of a natural airway region (e.g., tracheal region). In some embodiments, the cross-section of a support is designed to prevent or reduce the likelihood that one or both ends of a structural component or rib would protrude from either side of a synthetic scaffold after implantation (e.g., due to physical stresses resulting from typical motion or other movement, for example coughing in a transplant recipient). In some embodiments, a cross-sectional shape shown in FIG. 1C reduces the protrusion risk of a structural component or rib that is placed or deposited over or incorporated into the convex, curvilinear perimeter region of the transverse cross-section shown in FIG. 1C, for example, all or part of the surface portion (the convex, curvilinear perimeter region) that connects the two ends of the flat, or substantially flat, perimeter region at the base of the cross-section. In FIG. 1C, the length of the substantially flat perimeter region is smaller than the maximum outer dimension of the convex, curvilinear region along an axis parallel to the flat perimeter region. In some embodiments, the rib or structural components is attached to the support such that the ends of each rib or component are positioned between the maximum outer dimension of the convex, curvilinear region and the substantially flat perimeter region, as depicted in FIG. 6. FIG. 6A illustrates a non-limiting embodiment of a cross-section (e.g., a transverse cross-section) of a structural component of a synthetic scaffold overlaid on a cross-section of a support. FIG. 6B illustrates a non-limiting embodiment of a side longitudinal view of several structural components of a synthetic scaffold along the length of a support. It should be appreciated that in some embodiments, a curvilinear segment that connects the flat or substantially flat base may comprise or consist of a curve or arc, a combination of two or more curves or arcs having different radii, one or more parabolic sections, one or more other convex shapes, or a combination of two or more thereof. In some embodiments, the curvilinear segment does not include any other flat portions other than the flat or substantially flat base segment that corresponds to the dorsal region of an airway scaffold. In some embodiments, these one or more features help distribute any potential physical stress, and reduces the likelihood that a portion of a structural component (e.g., an end of an open loop) or rib will protrude from the side of the scaffold.

In some embodiments, the cross-section comprises features that can be easily scaled to accommodate differences in target tissue sizes, e.g., tracheal sizes, in different patients. In some embodiments, a cross-sectional profile is selected for a support that can be easily scaled by specifying the height (a) and width (b) of a bounding box around the cross section, as depicted, for example, in FIG. 1E. Examples of suitable cross sections are provided in FIG. 1. Thus, in some embodiments, a surgeon or other healthcare provider can obtain measurements of height (a) and width (b) of a target tissue (e.g., trachea) to be removed and replaced. These measurements can then be used to select or obtain an appropriately scaled support for producing the replacement tissue. This methodology is advantageous for producing tissue scaffolds having one or more regions having similar cross-sectional geometries (even if they have different sizes), e.g., having cross sections similar to that depicted in FIG. 1C, for example (or any other cross-section described herein). In some embodiments, this methodology is suitable for producing synthetic structures to replace one or portions of diseased (e.g., cancerous or otherwise diseased) or injured airway regions, including subglottic tissues, tracheal tissues, bronchial tissues, other tissues, and combinations thereof, and transition regions between these tissues. A transition region can have any suitable shape, it can be tapered, convex, concave, linear, or any other suitable shape. In some embodiments, two or more different regions of a support have different cross-sections, for example to produce first and second regions of a synthetic scaffold that have different cross sections (e.g., corresponding to adjacent regions in a patient that are being replaced, for example if a lesion or wound being treated by tissue transplantation encompasses at least a portion of each of two adjacent regions having different cross-sectional geometries). In some embodiments, each of the first and second regions can have a cross-section that is independently selected from the cross-sections shown in FIG. 1. In some embodiments, the first region of the support has the shape of FIG. 1C and the second region of the support has the shape of 1A, as shown in FIG. 2.

In some embodiments, the first and second regions have different sizes (e.g., one or both of the minor and major axes have different lengths in the first and second regions). In some embodiments, the second region has a larger diameter than either of the minor or major axes of the first region.

In some embodiments, the support includes a third region, attached to either the first or second region. The third region can be a rotating pin as illustrated in FIG. 2. The rotating pin can be used, for example, to attach the support to a device for fabricating an artificial scaffold (e.g. an electrospinning device). In some embodiments, the rotating pin has a circular cross-section. In some embodiments, the diameter of the rotating pin is smaller than that of either axis of either the first region or the second region.

Figure 3:
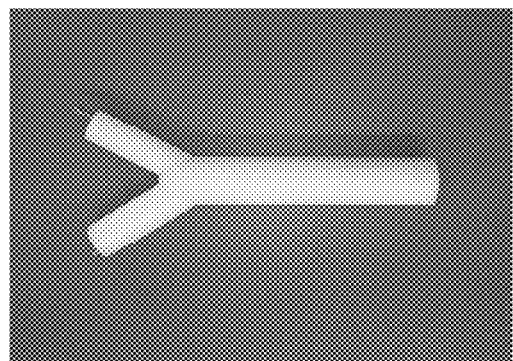
FIG. 3 is a photographic image of a bifurcated support for an artificial tissue scaffold.

In some embodiments, the support can be branched. In some embodiments, the support is bifurcated as shown in FIG. 3. In some embodiments, the support branching is symmetrical. In some embodiments, the support branching is asymmetrical. In some embodiments, one or more branches of a branched or bifurcated support is readily detachable from an elongate portion of the support in order to facilitate removal of the support from the scaffold after the scaffold is assembled on the support.

In some embodiments, the support is used to create an artificial scaffold that will partially or entirely replace a portion of an airway (e.g., a portion of a trachea). For example, the support of FIG. 2 can be used to create a scaffold that will be populated with cells to create an artificial airway region that can include a portion of a trachea and a portion of a subglottic region.

In some embodiments, the size and shape of the support is larger than the tissue being replaced. For example, the support can be 2%, 5%, 6%, 7%, 8%, 9%, 10%, or more, larger than the tissue being replaced. In some embodiments, the length of the diameter or of either the minor and/or major axis of the support cross-section can be designed to be longer than the corresponding length of the tissue (e.g., tracheal tissue) that is being replaced in a host. This allows for shrinkage of the scaffold that is produced on the support. For example, artificial scaffolds (e.g., polymer-based scaffolds, nanofiber-based scaffolds, for example PET-based scaffolds) that are prepared on a support can shrink (e.g., by 5-10%, for example 8%) after they are removed from the support.

Figure 1E:
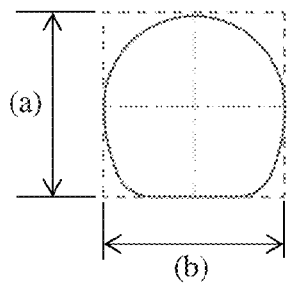
Figure 2A:
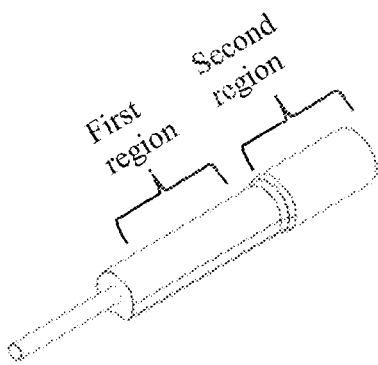
FIG. 2A is a non-limiting schematic drawing of a support for an artificial tissue having regions of different cross sectional geometry.
Figure 2B:
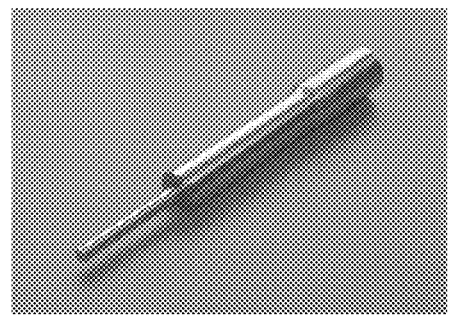
FIG. 2B is a photographic image of a support for an artificial tissue regions of different cross sectional geometry.

In some embodiments, the major axis of a support cross-section corresponds to the height (a), and the minor axis corresponds to the width (b) of a bounding box encompassing the cross section (See, e.g., FIG. 1E). However, in some embodiments, the minor axis of a support cross-section corresponds to the height (a), and the major axis corresponds to the width (b) of a bounding box encompassing the cross section.

It should be appreciated that the support can be longer in any direction (e.g., along any axis) relative to the tissue structure that is being replaced in a patient. In some embodiments, the support is a tubular structure that is longer on the longitudinal axis than the tissue being replaced. In some embodiments, at least a portion of the additional length can be designed for use during scaffold production (e.g., for attachment to a bioreactor) and/or surgery (e.g., to provide sufficient tissue for suturing). In some embodiments, a portion of the additional length can be used for biopsy sampling to evaluate or determine one or more properties of the scaffold (for example, to evaluate whether the scaffold is sufficiently cellularized prior to implantation, or to determine or confirm the identity of the cells that are on the scaffold). In some embodiments, all dimensions of the support are increased proportionately.

In some embodiments, supports are constructed of one or more wooden, plastic, polymeric, resin, metallic, carbon-based, or any other natural or synthetic material, or any combination of two or more thereof. In some embodiments, natural or synthetic supports (e.g., wooden or plastic supports) are coated with a conductive material (e.g., containing one or more metals) to that the surface is conductive (e.g., so that they can be used for electrospinning to deposit one or more fibers e.g., nanofibers, on the support). In some embodiments, supports are constructed entirely of a metal that is conductive (e.g., steel, or other metal, or a suitable alloy). Conductive supports can be used, for example, in electrospinning. It should be appreciated that the support can be hollow or solid. In some embodiments, the support can have surface grooves and/or pores (e.g., having depths, diameters, and/or cross sections of 1 micron-100 microns, or smaller or larger). Accordingly, the support can be made of, or include, one or more electrically conductive materials, e.g., materials suitable for serving as a collector for an electrospinning process. Accordingly, supports can be made from a metallic material or it can be coated with a metallic material, for example a metal layer or sheet (e.g., an aluminum layer or sheet). In some embodiments, the support is a composite comprising one or more electrically conductive materials, in which the electrically conductive materials are arranged or dispersed in a manner suitable for controlling the electrical conductivity of the support. In some embodiments, the support is made of a rigid material. In some embodiments, the support is made of a viscoelastic material.

In some embodiments, an artificial or synthetic scaffold can be formed by depositing electrospun fibers on the support. In some embodiments, support structures having different patterns of conductivity on their surface can be used to generate different patterns of fiber deposition.

In some embodiments, a tissue scaffold incorporates one or more cartilaginous structures. Accordingly, in some embodiments, a scaffold or a portion thereof is designed to replace one or more cartilaginous structures in a subject (e.g., a cricoid cartilage or a carina cartilage in the airway). Accordingly, in some embodiments, a scaffold or portion thereof is rigid. However, in some embodiments, the scaffold is not so rigid that it cuts or damages tissue. In some embodiments, the scaffold is configured with suitable geometric and mechanical properties so as not limit anatomical movement, such as coughing, bending, beyond physiologically acceptable ranges. In some embodiments, a scaffold or a portion of a scaffold has the rigidity of cartilage (e.g., cricoid cartilage). In some embodiments, the scaffold comprises both cartilaginous and non-cartilaginous regions with differing rigidities. It should be appreciated thickness the scaffold can vary.

It should be appreciated that in some embodiments scaffolds that are produced on supports described herein are tubular. It should be appreciated that a tubular region can be a cylinder with a uniform diameter. However, in some embodiments, a tubular region can have any appropriate tubular shape (for example, including portions with different diameters along the length of the tubular region and different cross-sectional shapes) based on the supports on which they are assembled. In some embodiments, a tubular scaffold can have one or more hollow regions. A tubular region also can include a branch or a series of branches. In some embodiments, a tubular scaffold is produced having an opening at one end, both ends, or a plurality of ends (e.g., in the case of a branched scaffold). In some embodiments, a synthetic structure that mimics a cartilaginous structure such as a cricoid cartilage can be produced as a separate synthetic scaffold portion in the form of a synthetic band or ribbon that can be placed over one or more layers of synthetic scaffold that has been deposited on a support as described herein. In some embodiments, the band or ribbon is circular (e.g., closed loop) and it is fed onto the support/scaffold from one or other end. In some embodiments, the band or ribbon is a flexible linear material and it is wrapped around the support/scaffold. This synthetic structure can be placed at or near a site that corresponds to the natural site of the corresponding natural cartilaginous structure. For example, in some embodiments, a synthetic cricoid structure is place on a synthetic scaffold at or near a position that corresponds to the natural position of the cricoid cartilage over the scaffold portion corresponding to the subglottic region and adjacent transition region connecting to a tracheal region.

In some embodiments, a scaffold or a subsection of a scaffold has the exact or nearly exact shape of the structure being replaced in a subject (e.g., a cricoid cartilage or carina cartilage in the airway).

Figure 4A:
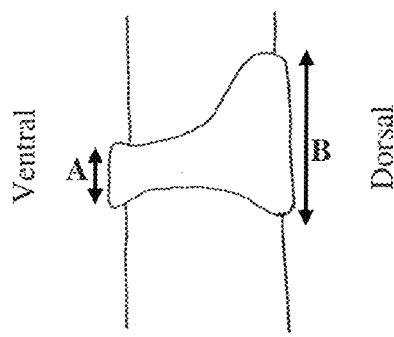
FIG. 4A is a non-limiting schematic drawing of natural cricoid cartilage depicting differences in height between the ventral portion (height A) and the dorsal portion (height B)
Figure 4B:
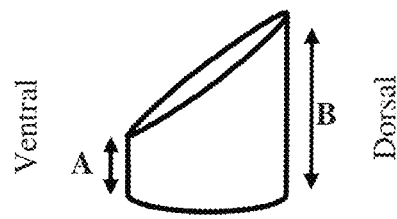
FIG. 4B is a non-limiting schematic drawing of a synthetic scaffold that includes a portion that mimics the cricoid cartilage of FIG. 4A, having similar differences in height between the ventral portion (height A) and the dorsal portion (height B)
Figure 5:
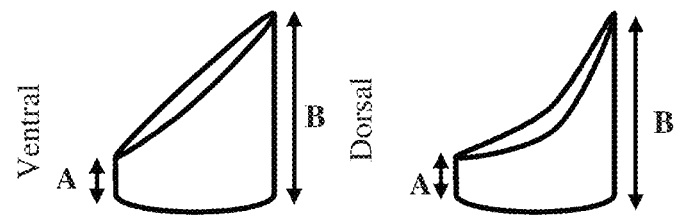
FIG. 5 is a schematic of synthetic scaffolds containing a cylindrical segment or truncated cylinder with variable side heights.
Figure 5:
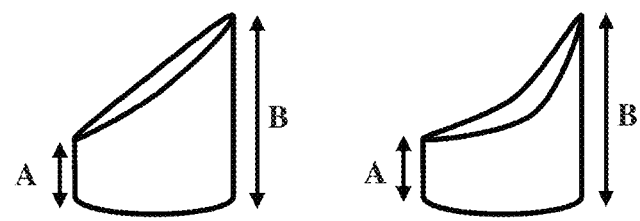
Figure 5:
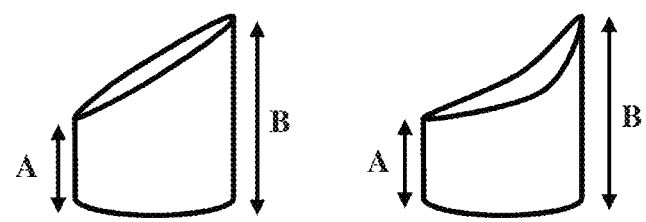

However, the manufacture of scaffolds with the exact shape or nearly exact shape of a complex host structure can be difficult. For example, a cricoid cartilage located in the airway has the complex structure shown in FIG. 4A with the dorsal side of the cartilage narrowing toward the ventral side and having a complex curvature. In some embodiments, the narrowing of the ventral side of the cricoid cartilage can prevent rubbing of the cricoid cartilage with the thyroid cartilage that sits above the cricoid cartilage. For manufacturing purposes, a synthetic scaffold that includes a portion that mimics the cricoid cartilage may focus on the ratio of the ventral to dorsal height of the natural cricoid cartilage (e.g., the ratio of A to B as shown in FIG. 4A and FIG. 4B) of a subject and not necessarily contain the complex curvature of the natural cricoid cartilage. Accordingly, in some embodiments, the scaffold does not have the exact shape of the structure being replaced, and instead has a synthetic structure that preserves the physiological properties of the structure. In some embodiments, the scaffold contains a cylindrical segment or truncated cylinder with variable side heights. In some embodiments the cylindrical segment or truncated cylinder has a ratio of A/B of approximately 1:1, 1:2, 1:3, 1:4, 1:5, 1:6, 1:7, 1:8, 1:9, 1:10, or greater. Examples of truncated cylinder side ratios are shown in FIG. 5. In some embodiments, the transition between the height of the dorsal and ventral side of the cylinder is exactly the same or approximately the same as the structure being replaced in the subject. In some embodiments, the transition between the height of the ventral and dorsal side (A to B) of the cylinder is linear (as in a truncated cylinder), exponential, logarithmic, polynomial, or a combination thereof. In some embodiments, the transition between the height of the ventral and dorsal side (A to B) of the cylinder comprises a concave portion, a convex portion or a combination of concave and convex portions.

Non-limiting examples of the transition between the height of the ventral and dorsal side (A to B) are shown in FIG. 5. In some embodiments, an artificial cricoid cartilage is designed to have the approximate size and shape of the cricoid cartilage that is being replaced in a patient. In some embodiments, the ratio of A/B of the patient cricoid cartilage is determined (e.g., using any suitable imaging technique) and a synthetic cricoid cartilage is produced to have the same or a similar ratio (e.g., within +/−5%-10% of the host dimensions). In some embodiments, the artificial cricoid cartilage is manufactured to have the overall size and shape of the patient cricoid cartilage. However, in some embodiments, the A/B ratio is maintained, but a simpler structure is manufactured.

In some embodiments, the scaffold contains a bifurcation. In some embodiments, the bifurcation is symmetrical. In some embodiments, the bifurcation is asymmetrical. It also should be appreciated that aspects of the invention may be used to produce scaffolds for any type or organ, including hollow and solid organs, as the invention is not limited in this respect.

In some embodiments, one or more regions of a scaffold (e.g., a structural component, a component that is designed to replace a cricoid cartilage, and/or other region of a scaffold) contains or includes cartilage. In some embodiments, the cartilage comprises elastic cartilage. In some embodiments, the cartilage comprises hyaline cartilage. In some embodiments, the cartilage comprises fibrocartilage. In some embodiments, the cartilage is taken from a subject (e.g., a human subject) as a biopsy (e.g., from the ear lobe or other inconspicuous part of the body e.g., internal cartilage (e.g., articular cartilage, costal cartilage or other connective tissue such as fat or muscle). In some embodiments, the cartilage taken by biopsy is used without further cell culture. In some embodiments, the cartilage taken by biopsy is modified to a specific shape and size. In some embodiments, cells or cellular material is extracted from the cartilage taken by biopsy material from the body and grown ex vivo for use in the scaffold. In some embodiments, the chondrocytes, pre-chondrocytes, mesenchymal stem cells or other suitable cells are isolated from cartilaginous tissue or another suitable tissue purposes of fabricating artificial cartilage. In some embodiments, fabricated cartilage is produced by culturing isolated chondrocytes or other suitable cells to produce cartilaginous sheets. Methods for fabricating cartilage from chondrocytes are known in the art.

In some embodiments, one or more regions of a scaffold contains or consists of artificial or synthetic material (e.g., alone or in combination with natural material such as natural cartilage). In some embodiments, the artificial or synthetic material consists of or includes electrospun material and/or a polymer mold. In some embodiments, a synthetic material (e.g., an artificial cartilage) may consist of or include double-network hydrogels. In some embodiments, a synthetic material (e.g., an artificial cartilage) may consist of or include one or more of the following materials: elastic polymers (e.g., one or more polyurethanes, for example polycarbonates and/or polyesters), acrylamide polymers, Nylon, resorbable materials (e.g., PLGA, PLA, PGA, PCL), synthetic or natural materials (e.g., silk, elastin, collagen, etc.) or any combination thereof. In some embodiments, a synthetic material (e.g., an artificial cartilage) may consist of or include addition polymer and/or condensation polymer materials such as polyolefin, polyacetal, polyamide, polyester, cellulose ether and ester, polyalkylene sulfide, polyarylene oxide, polysulfone, modified polysulfone polymers and mixtures thereof. In some embodiments, the scaffold may consist of or include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (e.g., 87% to 99.5%) in crosslinked and non-crosslinked forms. In some embodiments, the artificial cartilage may consist of or include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun to produce a synthetic material (e.g., an artificial cartilage) for one or more scaffold components described herein. In some embodiments, highly crystalline polymers like polyethylene and polypropylene may be solution spun to produce a synthetic material (e.g., an artificial cartilage). Methods of electrospinning polymers are known in the art. Electrospinning is a versatile technique that can be used to produce either randomly oriented or aligned fibers with essentially any chemistry and diameters ranging from nm scale (e.g., around 15 nm) to micron scale (e.g., around 10 microns). However, other techniques may be used, including "air laid" methods such as melt blowing, melt spinning, and gas jet fibrillation. In some embodiments, different gradients of fibers, deposition conditions, solvents, curing conditions, etc., or any combination thereof may be used to obtain patterns of fibers that result in a scaffold.

Accordingly, one or more components of a synthetic scaffold described herein can be made from synthetic materials, natural materials (e.g., decellularized tissue), or any suitable combination of two or more thereof. Further examples of suitable natural materials include hyaluronic acid, chitosan, collagen, chondroitin sulfate (CS) and others. In some embodiments, the scaffold may comprise donor, decellularized cricoid cartilage rings or other suitable anatomical features of an airway or target tissue.

It should be appreciated that different materials can be used in methods and compositions described herein. In some embodiments, the material is biocompatible so that it can support cell growth. In some embodiments, the material is permanent (e.g., PET), semi-permanent (e.g., it persists for several years after implantation into the host, or rapidly degradable (e.g., it is resorbed within several months after implantation into the host).

In some embodiments, a scaffold contains at least two different regions. In some embodiments, the first region is made of a different material than the second region. In some embodiments, the first region has a different structure than the second region. In some embodiments, the first region has a larger solid diameter than the second region. In some embodiments, the scaffold has alternating regions of larger and smaller solid diameters (e.g. mimicking the cartilaginous ribs with intervening tissue in the trachea) in one or both regions.

In some embodiments, the scaffold produced using a support involves placing a first structure or set of structures on the support and placing a second structure or set of structures on the support. In some embodiments, the first set of structures consists of cartilaginous structures. Cartilaginous structures are described herein. In some embodiments, a second structure or second set of structures are electrospun onto the support and on top of the first set of structures. For example, cartilaginous structures (e.g., strips of cartilaginous material) are placed or deposited on a support with space between the cartilaginous structures (e.g., mimicking the ribs of the trachea). In some embodiments, polymers are electrospun to cover both the cartilaginous structures and the space not occupied by the cartilaginous structures on the support. In some embodiments, an initial layer of synthetic material is placed or deposited (e.g., electrospun) onto the support before placing the first structure or set of structures (e.g., a synthetic cartilage, for example to replace a cricoid cartilage, and/or one or more structural elements such as ribs as described herein) onto this initial layer. In some embodiments, a second layer of synthetic material is placed or deposited (e.g., electrospun) over the initial layer and the one or more structures. The resulting scaffold can be used to mimic the structure of an airway region (e.g., a tracheal region and/or a subglottic region). In some embodiments, a treatment is applied to the scaffold during or after production to enhance adhesion between the first set of structures and the second set of structures. In some embodiments, the treatment involves, e.g., chemicals, temperature changes (e.g., heating), or vacuum plasma surface activation. In some embodiments, the edges of the first set of structures (e.g., cartilaginous strips), are treated to reduce tearing or degradation of the second set of structures (e.g., electrospun fibers overlaying the cartilaginous strips). In some embodiments, treatment involves, e.g., chemicals, temperature changes (e.g. heating), or abrasion.

Accordingly, in some embodiments, a structural scaffold element may be added over a first layer of scaffold. For example, a first layer of tubular tracheal scaffold may be deposited on a support (e.g., a mandrel) using any suitable technique (e.g., electrospinning, or other technique) and one or more structural scaffold elements (e.g., synthetic ribs of any suitable size and shape) can be placed or deposited over the first layer. The one or more structural scaffold elements can be attached to first layer using any suitable technique. Structural scaffolds can have any suitable size or shape. The size and shape will depend on the portion of the airway and the size of the patient. Non-limiting examples of artificial structural scaffolds include C-shaped and D-shaped tracheal ribs, tracheal ribs having cross-sections corresponding to the cross-section of a support as described herein (e.g., as illustrated in FIGS. 1 and/or 6), and an artificial cricoid cartilage as described herein. It should be appreciated that the artificial cricoid cartilage can have any suitable size depending on the patient (e.g., from about 0.5 cm to about 5 cm, but any size that corresponds to a patient size may be used). In some embodiments, an artificial cricoid cartilage has an internal diameter that is similar or slightly larger than the external diameter of the artificial airway to make it easier to place the cricoid cartilage in the appropriate position on the outside of the artificial airway.

It should be appreciated that scaffolds can be prepared under sterile conditions and/or sterilized after production so that they are suitable for cellularization. In some embodiments, complete sterilization is not required and manufacturing can be under controlled microbiological load (e.g., with about 1,000 bacteria per scaffold). However, any suitable sterilization techniques may be used. In some embodiments, scaffolds are gamma sterilized.

It should be appreciated that the types of cells that are used for cellularization will depend on the tissue type that is being produced. In some embodiments, one or more different tissue-specific (e.g., tissue-specific stem or progenitor) cells may be used. In some embodiments, different combinations of epithelial, endothelial, and/or structural cell types may be used to populate a scaffold. In some embodiments, cells are selected to be compatible (e.g., histocompatible) with the host into which the scaffold is being transplanted. In some embodiments, one or more cell types that are isolated from the host are used to seed the scaffold. In some embodiments, the seeded scaffold is incubated to allow the cells to grow and further populate the scaffold prior to surgical implantation.

It should be appreciated that cell types used to seed a scaffold of the invention may be selected based on the type of structure (e.g., tissue, organ) that is being produced. In some embodiments, the cells may be epithelial, endothelial, mesothelial, connective tissue cells, fibroblasts, etc., or any combination thereof. In some embodiments, the cells may be stem cells, progenitor cells, mesenchymal stem cells, induced pluripotent stem cells, stromal cells, fibroblasts, chondrocytes, chondroblasts, etc., or any combination thereof. These cells can be readily derived from appropriate organs or tissue such as skin, liver, blood, etc., using methods known in the art. In some embodiments, the cells are marrow derived cells, e.g., cells derived from red marrow. Thus, in some embodiments, a bone marrow extraction procedure may be performed on a subject to obtain cells suitable for seeding a scaffold for producing a tissue to be implanted in the subject. However, in some embodiments, the marrow cells, or other cells, to be used are obtained from a donor, as the invention is not limited in this respect.

It should be appreciated that the number of cells required to cellularize a scaffold as described herein will depend on the size of the scaffold, which will depend on the size of the tissue being replaced. It should also be appreciated that scaffolds may be seeded with cells using any of a variety of methods that permit cells to attach to the scaffold. For example, cells suspended in a medium (e.g., a cell culture medium) may be washed or poured over or sprayed onto a scaffold (or applied to the scaffold by another suitable technique) for a sufficient duration and in sufficient quantities to permit cells to contact and attach to the scaffold. In some embodiments, a scaffold may be bathed in a cell culture bath to seed cells on the scaffold. In some embodiments, a scaffold may be rotated in a cell culture bath such that cells from the bath contact and attach to the scaffold. In some embodiments, the scaffold is stationary within a cell culture bath, and the culture fluid is circulated around or over the scaffold. In some embodiments, a culture fluid is replaced periodically in a batch mode or can be continuously perfused into and out from the bath. However, it should be appreciated that any suitable cell seeding technique may be used. In some embodiments, the scaffold may be seeded uniformly. In some embodiments, cells are seeded non-uniformly over the scaffold, e.g., by pouring cells over one or more different regions of the scaffold. Additional methods for seeding cells on a scaffold are disclosed, for example, in United States Patent Application Publication No. 20110033918, entitled Rotating Bioreactors, the contents of which are incorporated herein by reference.

In some embodiments, different cells may be used to seed the outer and inner surfaces of a tubular structure (e.g., to form different inner and outer layers that correspond, at least in part, to natural inner and outer layers of a natural body structure). In some embodiments, different cells may be used to seed different sections that need to have different biological properties. For example, chondrocytes or chondroblasts may be used to seed a region of the scaffold to produce artificial cartilage (e.g., to create a region similar to the cricoid cartilage of the trachea), while another cell type may be used to produce a non-cartilaginous region of the scaffold. In some embodiments, only the inner or the outer surface of the support is seeded with cells.

In some embodiments, surface properties of the scaffold can be modified before seeding, during seeding, or after implantation. In some embodiments, the surface is treated with vacuum plasma surface activation. In some embodiments, vacuum plasma surface activation treatment is used to sterilize the scaffold, to enhance cell attachment to the scaffold, to enhance cell infiltration into the scaffold, or any combination thereof. It should be appreciated that other techniques may be used to sterilize a scaffold prior to seeding with cells.

It should be appreciated that these techniques described herein may be used alone or in combination. It also should be appreciated that the following techniques also may be used, either alone or in combination (for example in combination with each other or with the techniques described above) to produce scaffolds having suitable biological properties.

What is claimed is:

1. A method of producing an artificial tissue scaffold, the method comprising;
   obtaining a support for an artificial tissue scaffold, the support including:
   a first solid tubular region having a substantially flat perimeter region;
   a second solid tubular region, connected to the first solid tubular region, wherein the second region has a transverse cross-section with radial symmetry; and
   an intermediate region located between the first solid tubular region and the second solid tubular region;
   wherein the first region has a different cross-section than the second region, and wherein a transverse cross-section of the first region has a convex curvilinear outer perimeter region interrupted by the substantially flat perimeter region, such that the first region has bilateral symmetry but not radial symmetry, and wherein an axis of bilateral symmetry passes perpendicularly through a midpoint of the substantially flat perimeter region;
   wherein the intermediate region has a cross-sectional size that is between the first region and the second region; and
   wherein the support is made partially or entirely of conductive metal; and
   depositing a synthetic or natural material on the obtained support, wherein the synthetic or natural material forms a scaffold having an inner size and shape corresponding to an outer surface of the support;
   wherein the synthetic or natural material is deposited on the support by electrospinning; and
   removing the support from the formed scaffold.

2. The method of claim 1 further comprises:
   seeding cells on the removed scaffold; and
   maintaining the cells on the scaffold under construction suitable for partially or completely cellularizing the scaffold.

3. The method of claim 1 wherein the scaffold obtained in the depositing step comprises:
   one or more structural ribs; and optionally wherein the scaffold comprises a plurality of ribs and wherein the plurality of ribs are spaced along a length of the support and further optionally wherein each rib is positioned on the support such that ends of each rib are positioned between a maximum outer dimension of the convex curvilinear outer perimeter region and the substantially flat perimeter region.

4. The method of claim 1 wherein the support further comprises a rotating pin projecting from either the first or second region of the cmbcr support, the rotating pin having a diameter less than an outer perimeter of the support from which the rotating pin projects.

* * * * *